(12) United States Patent
Schmidt

(10) Patent No.: US 9,827,436 B2
(45) Date of Patent: Nov. 28, 2017

(54) SYSTEMS AND METHODS TO IMPROVE THE GROWTH RATE OF LIVESTOCK, FISH, AND OTHER ANIMALS

(71) Applicant: Medical Energetics Ltd., Galway (IE)

(72) Inventor: David G. Schmidt, Poway, CA (US)

(73) Assignee: Medical Energetics Ltd., Galway (IE)

( * ) Notice: Subject to any disclaimer, the term of this patent is extended or adjusted under 35 U.S.C. 154(b) by 290 days.

(21) Appl. No.: 14/636,142

(22) Filed: Mar. 2, 2015

(65) Prior Publication Data

US 2016/0256249 A1    Sep. 8, 2016

(51) Int. Cl.
| A61N 2/00 | (2006.01) |
| A61N 2/02 | (2006.01) |
| A01K 29/00 | (2006.01) |
| A61D 99/00 | (2006.01) |

(52) U.S. Cl.
CPC .............. *A61N 2/004* (2013.01); *A01K 29/00* (2013.01); *A61N 2/02* (2013.01); *A61D 99/00* (2013.01)

(58) Field of Classification Search
CPC .......... A61N 2/00; A61N 2/002; A61N 2/004; A61N 2/006; A61N 2/008; A61N 2/02; A61N 2/06; A61N 1/40; H01F 5/00; H01F 7/06; H01F 7/20
See application file for complete search history.

(56) References Cited

U.S. PATENT DOCUMENTS

| 1,898,661 | A | 2/1933 | Hagen | |
| 2,035,274 | A | 3/1936 | Mougey | 173/265 |
| 3,066,295 | A | 11/1962 | Krause et al. | 343/874 |
| 3,760,812 | A | 9/1973 | Timm et al. | 128/418 |
| 3,774,452 | A | 11/1973 | Tullos et al. | 73/418 |
| 4,266,532 | A | 5/1981 | Ryaby et al. | 128/1.5 |
| 4,439,702 | A | 3/1984 | Belikov et al. | 310/80 |
| 4,489,276 | A | 12/1984 | Yu | 324/338 |
| 4,832,051 | A | 5/1989 | Jarvik et al. | 128/784 |
| 5,077,934 | A | 1/1992 | Liboff et al. | 47/1.3 |
| 5,079,458 | A | 1/1992 | Schuster | 310/12 |
| 5,173,669 | A | 12/1992 | Manoly | 333/162 |
| 5,182,537 | A | 1/1993 | Thuis | |
| 5,339,061 | A | 8/1994 | Reick | |
| 5,359,340 | A | 10/1994 | Yokota | 343/792 |
| 5,366,493 | A | 11/1994 | Scheiner et al. | 607/116 |
| 5,464,456 | A | 11/1995 | Kertz | 47/1.3 |
| 5,654,723 | A | 8/1997 | Craven et al. | 343/742 |
| 5,819,467 | A | 10/1998 | Zucker | 47/1.3 |
| 5,892,480 | A | 4/1999 | Killen | 343/385 |
| 5,909,165 | A | 6/1999 | Leupold | 335/210 |
| 5,954,630 | A | 9/1999 | Masaki et al. | 600/28 |
| 5,977,932 | A | 11/1999 | Robinson | |
| 6,005,462 | A | 12/1999 | Myers | 335/220 |

(Continued)

FOREIGN PATENT DOCUMENTS

| GB | 479841 | 2/1938 |
| GB | 2480610 | 11/2011 |

(Continued)

*Primary Examiner* — Charles A Marmor, II
*Assistant Examiner* — Carrie R Dorna
(74) *Attorney, Agent, or Firm* — ARC IP Law, PC; Joseph J. Mayo

(57) ABSTRACT

An electrical system having an underlying structure having a helical shape is used to produce useful electromagnetic effects for agricultural applications, including promoting growth of animals.

29 Claims, 3 Drawing Sheets

(56) References Cited

U.S. PATENT DOCUMENTS

| | | | |
|---|---|---|---|
| 6,169,523 B1 | 1/2001 | Ploussios | 343/895 |
| 6,239,760 B1 | 5/2001 | Van Voorhies | 343/742 |
| 6,300,920 B1 | 10/2001 | Pertl et al. | 343/895 |
| 6,552,530 B1 | 4/2003 | Vaiser et al. | 324/204 |
| 6,770,023 B2 | 8/2004 | Vaiser et al. | 600/13 |
| 6,921,042 B1 | 7/2005 | Goodzeit et al. | 242/430 |
| 6,978,179 B1 | 12/2005 | Flagg | |
| 7,148,783 B2 | 12/2006 | Parsche et al. | 336/225 |
| 7,154,368 B2 | 12/2006 | Sweeney et al. | 336/229 |
| 7,375,449 B2 | 5/2008 | Butterfield | 310/207 |
| 8,463,407 B2 | 6/2013 | Bulkes et al. | 607/148 |
| 8,652,023 B2 | 2/2014 | Schmidt | 600/13 |
| 8,653,925 B2 | 2/2014 | Schmidt | 336/188 |
| 8,749,333 B2 | 6/2014 | Schmidt | 336/73 |
| 8,919,035 B2 | 12/2014 | Schmidt | 47/1.3 |
| 8,961,384 B2 | 2/2015 | Schmidt | |
| 9,030,283 B2 | 5/2015 | Schmidt | |
| 2003/0169132 A1 | 9/2003 | Vaiser | |
| 2005/0121396 A1 | 6/2005 | Kosakewich | 210/748 |
| 2008/0161884 A1 | 7/2008 | Chandler et al. | 607/50 |
| 2008/0266203 A1 | 10/2008 | Rossetto et al. | 345/895 |
| 2009/0206974 A1 | 8/2009 | Meinke | 336/224 |
| 2009/0260849 A1 | 10/2009 | Cardas | |
| 2010/0005711 A1 | 1/2010 | McNeff | 47/1.4 |
| 2010/0057655 A1 | 3/2010 | Jacobson et al. | 706/45 |
| 2010/0113862 A1 | 5/2010 | Kotowich | |
| 2010/0152811 A1 | 6/2010 | Flaherty | |
| 2010/0160713 A1* | 6/2010 | Cuppen | A61N 2/02 600/14 |
| 2010/0179630 A1 | 7/2010 | Williams | 607/127 |
| 2012/0101366 A1 | 4/2012 | Ruohonen | |
| 2012/0143285 A1 | 6/2012 | Wang | |
| 2012/0223800 A1 | 9/2012 | Schmidt | 336/229 |
| 2013/0192129 A1 | 8/2013 | Schmidt | 471/1.3 |
| 2013/0211181 A1 | 8/2013 | Schmidt | 600/13 |
| 2013/0285782 A1 | 10/2013 | Schmidt | 336/73 |
| 2014/0097925 A1 | 4/2014 | Schmidt | 336/188 |
| 2014/0100412 A1 | 4/2014 | Schmidt | 600/13 |
| 2014/0218149 A1 | 8/2014 | Schmidt | 336/73 |
| 2014/0371514 A1 | 12/2014 | Schmidt | 600/13 |
| 2015/0119630 A1 | 4/2015 | Schmidt | |
| 2015/0119631 A1 | 4/2015 | Schmidt | |
| 2015/0119632 A1 | 4/2015 | Schmidt | |
| 2015/0157871 A1 | 6/2015 | Schmidt | |
| 2015/0283393 A1 | 10/2015 | Schmidt | |
| 2015/0283394 A1 | 10/2015 | Schmidt | |

FOREIGN PATENT DOCUMENTS

| | | |
|---|---|---|
| WO | WO 2012/118971 | 9/2012 |
| WO | WO 2013/112810 | 8/2013 |
| WO | WO 2013/123009 | 8/2013 |

* cited by examiner

SYSTEMS AND METHODS TO IMPROVE THE GROWTH RATE OF LIVESTOCK, FISH, AND OTHER ANIMALS

FIELD OF THE INVENTION

The invention relates to bodies structured as one or more helically wound runners around which one or more conductive wires may be wound, electrical devices and/or systems configured to include such bodies, and agricultural applications thereof.

BACKGROUND OF THE INVENTION

It is known that spirally wound electrical conductors exhibit certain electromagnetic properties and/or can be used, e.g., to generate particular electromagnetic fields. For example, it is known that an electromagnetic coil may act as an inductor and/or part of a transformer, and has many established useful applications in electrical circuits. Applications of an electromagnetic coil may exploit the electromagnetic field that is created when, e.g., an active current source is operatively coupled to the coil.

SUMMARY

One aspect of the invention relates to an electrical system for promoting growth of life stock, fish, and/or other animals. The system includes one or more bodies, one or more runners, one or more conductive wires, one or more current sources, and/or other components. Individual bodies may include one or more runners arranged in a helical shape having at least two complete revolutions per runner. Individual bodies may have a periphery. Individual bodies may be installed around and/or near one or more animals. Individual wires may be carried by individual runners. Individual wires may be conductive. Individual current sources may be arranged to electrically couple with one or more wires causing one or more currents through one or more wires. The one or more current sources may be configured to cause currents through wires such that one or more electromagnetic effects, e.g. electromagnetic fields, are created in and/or around individual bodies. The one or more electromagnetic effects may promote growth of the one or more animals disposed within and/or near the one or more bodies.

One aspect of the invention relates to a method for promoting growth of life stock, fish, and/or other animals. The method may include installing one or more bodies around and/or near one or more animals and supplying one or more currents to the one or more bodies such that one or more electromagnetic effects, e.g. electromagnetic fields, are created within and/or near the body. The one or more electromagnetic effects may promote of growth of the one or more animals within and/or near the one or more bodies. Individual bodies may include one or more runners, one or more wires, and/or other components. Individual runners may be arranged in at least two complete revolutions per runner. Individual wires may be carried by individual runners. Individual wires may be conductive. The one or more current sources may be configured to supply currents through individual wires such that one or more electromagnetic effects, e.g. electromagnetic fields, are created in and/or around one or more bodies.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
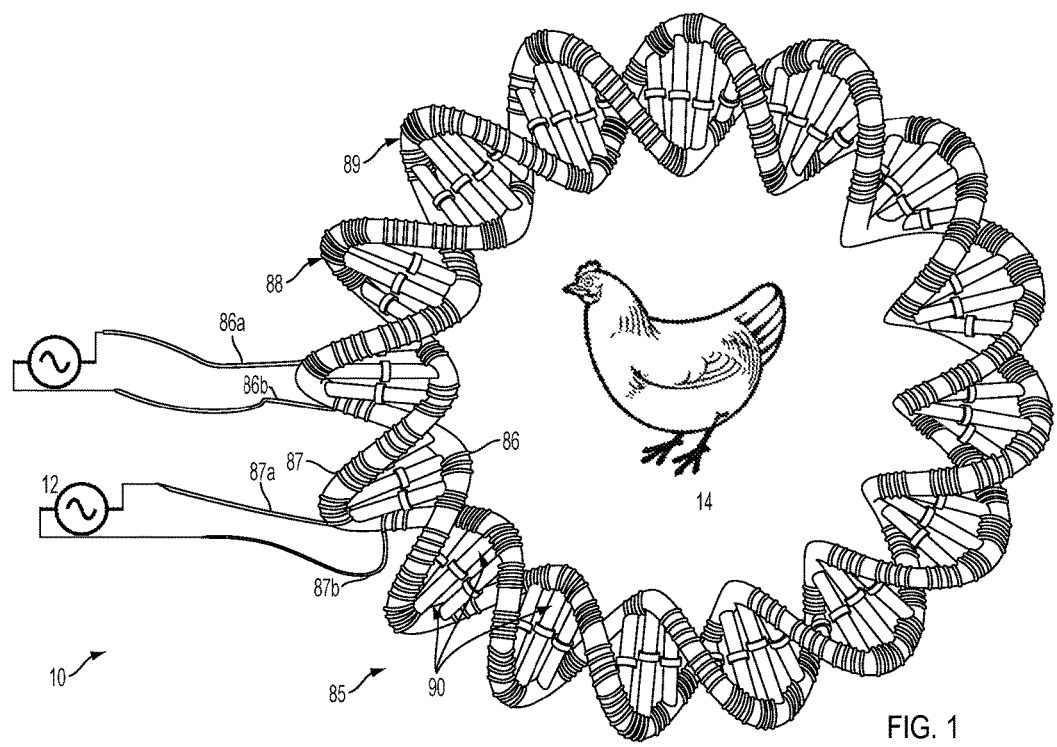
FIG. 1 schematically illustrates a system for promoting growth of an animal, according to one or more implementations.

FIG. 1 illustrates a system 10 for promoting growth of an animal 14, according to one or more implementations. System 10 includes a body 85, a first wire 86, a current source 11, and/or other components. The depiction of animal 14 as a single entity is not meant to be limiting. Animal 14 may include one or more animals and/or other organisms. As used herein, the term "animal" may refer to any organism of the kingdom Animalia except humans. In some implementations, system 10 may be configured to promote growth in livestock, fish, and/or other animals. In some implementations, system 10 may be configured to promote growth of animals that are raised, bred, grown, or produced in captivity and/or under human control. In some implementations, system 10 may be configured to promote growth of animals for a commercial purpose, including but not limited to the purpose of human consumption. In some implementations, the term animal may include genetically modified and/or synthetic organisms. In some implementations, an animal may include, by way of non-limiting example, a chicken, a cow, a pig, a lamb, a goat, a bird, a fish, a crustacean, a mollusk, a reptile, and/or other animals.

By way of non-limiting example, additional structures and/or features of body 85, runners 88 and 89, current source 11, and/or processing component described herein, may be described in U.S. Pat. No. 8,653,925, entitled "Double Helix Conductor," which issued Feb. 18, 2014, which is hereby incorporated into this disclosure by reference in its entirety. This patent may also be referred to as "the '925 patent" herein.

By way of non-limiting example, additional structures and/or features of body 85, runners 88 and 89, current source 11, and/or processing component described herein, may be described in U.S. Pat. No. 8,919,035, entitled "Agricultural Applications of a Double Helix Conductor," which issued Dec. 30, 2014, which is hereby incorporated into this disclosure by reference in its entirety. This patent may also be referred to as "the '035 patent" herein.

By way of non-limiting example, additional structures and/or features of body 85, runners 88 and 89, current source 11, and/or processing component described herein, may be described in U.S. patent application Ser. No. 14/194,412, entitled "HEALTH APPLICATIONS FOR USING BIO-FEEDBACK TO CONTROL AN ELECTRO-MAGNETIC FIELD," which was filed Feb. 28, 2014, which is hereby incorporated into this disclosure by reference in its entirety. This patent may also be referred to as "the '412 application" herein.

Body 85 of system 10 in FIG. 1 may include one or more helically wound runners. As depicted in FIG. 1 by way of non-limiting example, body 85 may include two intertwined helically wound runners—runner 88 and runner 89—sharing the same (circular) axis. Runner 88 and runner 89 may be arranged in the shape of a double helix. Individual runners may be coupled by struts 90 to other runners. Individual ones of the runners may have one or more conductive wires spirally wound therearound. Runner 88 and runner 89 of body 85 may form cores around which wire 86 and wire 87 are spirally wound, respectively. As depicted in FIG. 1, body 85 includes two wires: wire 86 and wire 87. In some implementations, system 10 includes one runner, three runners, and/or another number of runners. In some implementations, system 10 includes one wire, three wires, and/or another number of wires. In some implementations, system 10 includes one current source, three current sources, and/or another number of current sources.

Wire 86, as any wire listed in any figure included in this description, may be insulated, uninsulated, or partially insulated and partially uninsulated. As used herein, any "wire" may include a set of twisted wires (which may interchangeably be referred to as a "twisted wire" or a "pair of twisted wires"), including but not limited to a set of two twisted wires. The number of turns of a set of twisted wires per inch and/or per helical revolution of a runner may be characteristic measurements/features of the system. In some implementations, the number of twists per inch of a twisted wire may be about 2, about 5, about 10, about 20, about 100, about 150, about 200, about 250, and/or another suitable number of twists. In some implementations, the number of twists per inch of a twisted wire may be 144 twists.

System 10 may include one or more current sources. As depicted in FIG. 1, system 10 may include two current sources, current source 11 and current source 12. Individual ones of the current sources may be configured to induce one or more currents through one or more wires and/or across electrical leads, including but not limited to the electrical leads of the one or more wires wound around the one or more runners of body 85. In some implementations, the one or more currents may include one or more alternating currents. In some implementations, one or more induced currents may correspond to one or more sensor-generated output signals. In some implementations, the one or more induced currents may correspond to one or more signals generated by a transducer, a signal generator, an (audio) amplifier, and/or other components, including but not limited to the components described in the '925 patent, the '035 patent, and/or the '412 application. In some implementations, the one or more current sources 12 may be configured to induce two independent currents to the two (twisted) wires that are spirally wound around the first runner and the second runner, respectively.

Runner 88 and runner 89 of body 85 and system 10 in FIG. 1 may be arranged in the shape of a three-dimensional curve similar to or substantially the same as a (double) helix, bend with its ends arranged together (e.g., in a toroidal shape). It is noted that the shape of body 85 resembles the general shape of DNA. The shape of the cross-section of a runner may include one or more of a circle, an oval, a square, a triangle, a rectangle, an angular shape, a polygon, and/or other shapes. The width and height of the cross-section of a runner may be limited for practical purposes. For example, for the purposes described herein, in some implementations, it may be preferred arrange body 85 such that there is available space within the periphery of body 85, as shown, e.g., in FIG. 1. As depicted in FIG. 1, the shape of the cross-section of runner 88 and runner 89 is a circle. Note that implementations of this disclosure are not intended to be limited by any of the given examples.

In some implementations, individual wires may be arranged around individual runners such that the individual wire is arranged at a fixed and/or constant distance from the individual runner and/or the surface of the individual runner, at least for one or more individual ones of the revolutions of the helical shape of the individual runner. In some implementations, the individual wire is arranged in continuous contact with the individual runner and/or the surface of the individual runner, at least for one or more individual ones of the revolutions of the helical shape of the individual runner.

Runner 88, runner 89 and/or struts 90 of system 10 in FIG. 1 may be manufactured from one or more of plastic, plastic plated with metals including copper, nickel, iron, soft iron, nickel alloys, and/or other metals and alloys, and/or other materials. In some implementations, runner 88, runner 89 and struts 90 may be manufactured from non-conductive material. Runner 88, runner 89, and struts 90 may be manufactured from different materials. Runner 88, runner 89, and struts 90 may be manufactured through integral construction or formed separately prior to being assembled. The preceding statement is not intended to limit the (process of) manufacture of bodies similar to or substantially the same as body 85 in any way. In some implementations, a body similar to body 85 may have no struts.

The shape of body 85 of system 10 in FIG. 1 may be generally toroidal. In some implementations, the body of system 10 may be arranged in any planar shape, including circular, polygonal, and/or other shapes. Alternatively, and/or simultaneously, a body such as body 85 may be arranged in a three-dimensional curve (a.k.a. space curve). Runner 88 and runner 89 of body 85 may form cores around which wire 86 and wire 87 are spirally wound, respectively. As such, wire 86 and wire 87 may be arranged in a helical shape having axes that coincide with runner 88 and runner 89, respectively. As shown in FIG. 1, wire 86 and 87 may be wound such that they go around any of struts 90 of body 85 and/or around any points of engagement between one of struts 90 and one of runners 88 and 89. The number of wire turns per complete revolution of a runner and/or the number of wire turns between adjacent struts may be characteristic measurements/features of body 85. In FIG. 1, wire 86 and wire 87 are arranged to make approximately three to five turns between adjacent struts associated with runner 88 and runner 89, respectively, and/or some other number of turns. The depiction of FIG. 1 is intended to be exemplary, and in no way limiting.

Wire 86 may include two or more leads—as depicted, lead 86a and lead 86b. Wire 87 may include two or more leads—as depicted, lead 87a and lead 87b. By way of non-limiting example, a twisted wire may have four leads. In system 10, body 85 is electrically coupled with one or more power sources and/or current sources, such as, e.g., current source 11 and/or a current source 12, arranged such that electrical coupling with one or both of wire 86 and wire 87 may be established, e.g. through coupling of current source 11 with lead 86a and 86b of wire 86 and through coupling of current source 12 with lead 87a and 87b of wire 87. The current supplied to wire 86 may be a direct current or an alternating current. The current supplied to wire 87 may be a direct current or an alternating current. The currents supplied to wire 86 and wire 87 may flow in the same direction or the opposite direction.

For alternating currents, operating frequencies ranging from 0 Hz to 100 GHz are contemplated. Operating currents ranging from 1 pA to 10 A are contemplated. Operating voltages ranging from 1 mV to 20 kV are contemplated. In some implementations, a root mean square voltage of about 12 V is supplied to wire 86 and/or wire 87. In a preferred implementation, the frequency of the alternating current supplied to wire 86 and/or wire 87 may be between 0 Hz and 20 kHz. In some implementations, the current is less than about 1 pA, 1 nA, 1 mA, 100 mA, 250 mA, 500 mA, and/or other amounts of current. The operating frequencies for wire 86 and wire 87 may be the same or different. Other electrical operating characteristics of current supplied to wire 86 and wire 87, such as phase, may be the same or different. System 10 may be used to exploit the electromagnetic effect and/or field that may be created in and/or around body 85 when electrical power is supplied to one or more wires of body 85. The electromagnetic effect may promote growth of animal 14 disposed within and/or near body 85 and/or the periphery of body 85.

Some implementations of a system including a body similar to or substantially the same as body 85 in FIG. 1, thus including wire 86 and wire 87, may be configured to have a current in wire 86 flowing in the opposite direction as the current in wire 87. In some implementations the current supplied to one wire may be a direct current, whereas the current supplied to another wire may be an alternating current.

Figure 3:
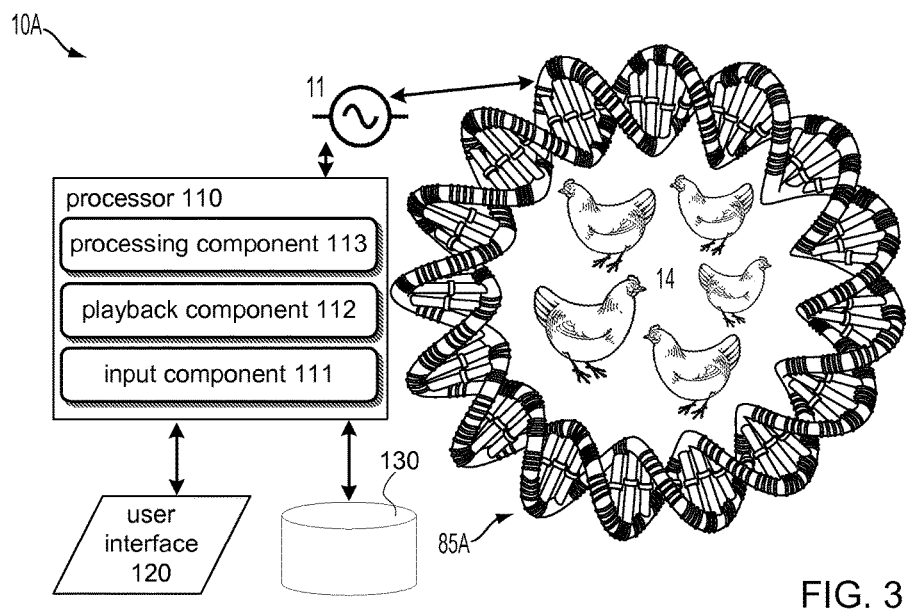
FIG. 3 illustrates a system for promoting growth of one or more animals, according to one or more implementations.

In some implementations, one or more currents flowing through a body similar to body 85 may be controlled to correspond to one or more signals. By way of non-limiting example, FIG. 3 illustrates a system 10A for promoting growth of one or more animals. System 10A may be the same as or similar to system 10 depicted in FIG. 1. System 10A may include a body 85A, a current source 11, one or more processors 110, a processing component 113, a playback component 112, an input component 111, a user interface 120, electronic storage 130, and/or other components. In some implementations, one or more components of system 10A may correspond to one or more processors, computer program components, user interfaces, electronic storage, and/or other components, including but not limited to the components described in the '925 patent, the '035 patent, and/or the '412 application.

System 10A may include a body 85A that is the same as or similar to body 85 depicted in FIG. 1. Body 85A may be suspended above the one or more animals 14, placed around the one or more animals 14, placed underneath an area for the one or more animals 14 (e.g. underneath a pen or other enclosure), and/or otherwise arranged in proximity of the one or more animals 14. In some implementations, body 85A may be installed around an area having a width between 10 and 500 feet, and having a length between 10 and 500 feet. In some implementations, the width may be about 4 feet, 6 feet, 8 feet, 10 feet, 15 feet, 20 feet, 25 feet, 30 feet, 40 feet, 50 feet, 75 feet, 100 feet, 150 feet, 200 feet, 250 feet, 300 feet, 400 feet, 500 feet, and/or another appropriate length that is suitable for the number and kind of animals disposed within and/or near body 85A. In some implementations, the length may be about 4 feet, 6 feet, 8 feet, 10 feet, 15 feet, 20 feet, 25 feet, 30 feet, 40 feet, 50 feet, 75 feet, 100 feet, 150 feet, 200 feet, 250 feet, 300 feet, 400 feet, 500 feet, and/or another appropriate length that is suitable for the number and kind of animals disposed within and/or near body 85A.

In some implementations, the one or more processors 110 may be configured to provide information-processing capabilities and/or execute computer program components, including but not limited to input component 111, playback component 112, processing component 113, and/or other components. Processor 110 may include one or more of a digital processor, an analog processor, a digital circuit designed to process information, a central processing unit, a graphics processing unit, an analog circuit designed to process information, and/or other mechanisms for electronically processing information. Although processor 110 is shown in FIG. 3 as a single entity, this is for illustrative purposes only. In some implementations, processor 110 may include a plurality of processing units.

In some implementations, an alternating current supplied to body 85A may include a carrier signal and a modulating signal. In some implementations, carrier signals used for the alternating current may be radio-frequency signals. As used herein, radio frequency may refer to frequencies between about 30 kHz and about 30 GHz. In some implementations, the modulating signal for the alternating current may be modulated through one or more of amplitude modulation, frequency modulation, phase modulation, digital modulation, and/or other types of modulation.

In some implementations, the one or more frequencies included in the alternating current may be based on audio recordings of a note, tone, or chord, generated by a frequency generator, a function generator, and/or a (musical) instrument. In some implementations, a first frequency may be used for the first runner, and a second frequency may be used for the second runner. For example, a first frequency may be based on the sound of an instrument, e.g. a piano, playing an A above middle C (also referred to as A4, which may include sound having a frequency of about 432 Hz, depending on the tuning system used). For example, a second frequency may be based on the sound of some instrument, e.g. a piano, playing a note forming a harmonious interval with A4, e.g. E5, which may include sound having a frequency of about 648 Hz. For example, a third frequency, if used, may be based on the sound of some instrument, e.g. a piano, playing a note forming a harmonious interval with A4, e.g. A5, which may include sound having a frequency of about 864 Hz. The particular tuning used in some implementations may be referred to as Pythagorean tuning. Mathematically perfect tuning may combine notes having a 3:2 ratio. Different types of tuning (or tuning systems), including but not limited to equal tempered tuning, may be used and considered within the scope of this disclosure.

It should be appreciated that although components 111-113 are illustrated in FIG. 3 as being co-located within a single processing unit, in implementations in which processor 110 includes multiple processing units, one or more of components 111-113 may be located remotely from the other components. The description of the functionality provided by the different components 111-113 described herein is for illustrative purposes, and is not intended to be limiting, as any of components 111-113 may provide more or less functionality than is described. For example, one or more of components 111-113 may be eliminated, and some or all of its functionality may be incorporated, shared, integrated into, and/or otherwise provided by other ones of components 111-113. Note that processor 110 may be configured to execute one or more additional components that may perform some or all of the functionality attributed below to one of components 111-113.

Input component 111 may be configured to obtain information, e.g. from one or more digital audio files, or, alternatively and/or simultaneously, based on sensor-generate output signals. In some implementations, the information may be obtained from storage, e.g. from electronic storage. Information obtained from storage may include electronic audio files in any format, including but not limited to MP3, WMA, WAV, AIFF, and/or other audio formats. In some implementations, information may be obtained from sound sources including frequency generators, function generators, phonographs, CD-players, DVD players, AM radio, FM radio, and/or other sound sources. In some implementations, the information obtained by input component 111 may be streaming data (e.g. streaming audio) from a particular website.

Processing component 113 may be configured to process the obtained information from input component 111. In some implementations, processing component 113 may be configured to generate a processed signal based on the obtained information from input component 111. For example, processing component 113 may convert, filter, modify, and/or otherwise transform information or signals from input component 111 to generate the processed signal.

Playback component 112 may be configured to produce sound signals based on one or more of the obtained information from input component 111 and/or the processed signal from processing component 113. The sound signals produced by playback component 112 may be coupled electrically to the leads of one or more conductive wires wound around one or more runners of body 85A such that the induced current may correspond to and/or be based on the sound signals. Alternatively, and/or simultaneously, the induced current may be controlled by and/or based on the sound signals produced by playback component 112. In some implementations, the sound signals produced by playback component 112 may be amplified by an amplifier (not shown) before being electrically coupled to the leads of one or more conductive wires. In some preferred implementations, the amplifier may be an audio amplifier ranging between 100 W and 400 W. Other types of amplifiers and/or amplifiers having a different power range are also contemplated.

Electronic storage 130 of system 10A in FIG. 3 may include electronic storage media that electronically stores information. The electronic storage media of electronic storage 130 may include one or both of system storage that is provided integrally (i.e., substantially non-removable) with its electrical system and/or removable storage that is connectable to its electrical system via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10A or another system described in this disclosure to function properly. For example, electronic storage 130 may store sound information and/or electronic audio files (as discussed elsewhere herein), and/or other information. Electronic storage 130 may be a separate component within its electrical system, or electronic storage 130 may be provided integrally with one or more other components of its electrical system (e.g., processor 110).

User interface 120 of system 10A in FIG. 3 may be configured to provide an interface between the system and a user through which the user can provide information to and receive information from the system. This enables data, results, and/or instructions and any other communicable items, collectively referred to as "information," to be communicated between a user and the system. An example of information that may be conveyed to a user is an indication of the volume and/or intensity of the sound signals produced by playback component 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to a user by user interface 120 in the form of auditory signals, visual signals, tactile signals, and/or other sensory signals.

It is to be understood that other communication techniques, either hard-wired or wireless, are also contemplated herein as user interface 120. For example, in one implementation, user interface 120 may be integrated with a removable storage interface provided by electronic storage 130. In this example, information is loaded into system 10A in FIG. 3 from removable storage (e.g., a smart card, a flash drive, a removable disk, etc.) that enables the user(s) to customize the system 10A. Other exemplary input devices and techniques adapted for use with system 10A may include, but are not limited to, an RS-232 port, RF link, an IR link, modem (telephone, cable, Ethernet, internet or other). In short, any technique for communicating information with system 10A FIG. 3 is contemplated as user interface 120.

Figure 4:
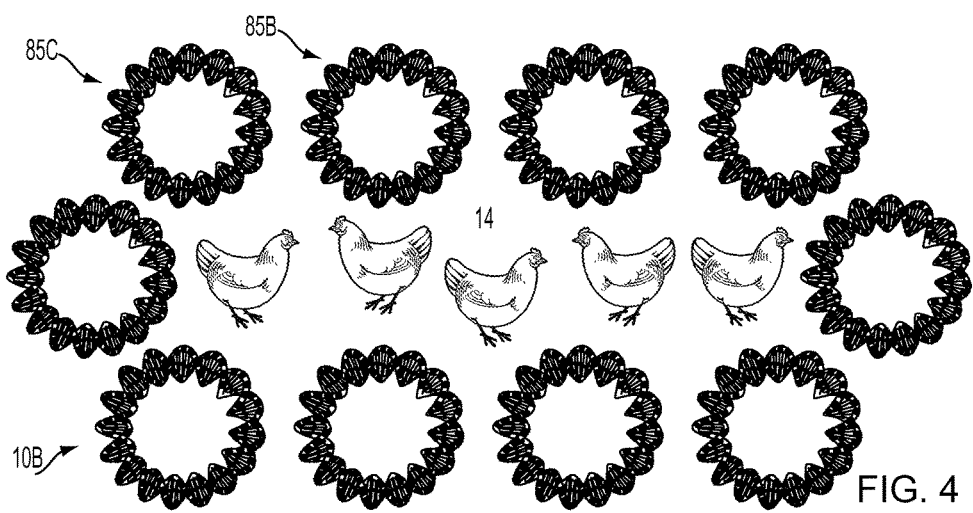
FIG. 4 illustrates a system for promoting growth of one or more animals, according to one or more implementations.

In some implementations, system 10 may include multiple bodies similar to or substantially the same as body 85. Currents for these multiple bodies may be supplied by one or more power sources and/or current sources. In some implementations, a system may include a combination of one or more bodies similar to or substantially the same as body 85 and one or more bodies similar to or substantially the same as body 85. By way of non-limiting example, FIG. 4 illustrates a system 10B for promoting growth of one or more animals. System 10B may be the same as or similar to system 10A depicted in FIG. 3. System 10B may include a set 85C of bodies 85B, and/or other components. By way of non-limiting example, one or more current sources, processors, computer program components, user interfaces, electronic storage, and/or other components are not depicted in FIG. 4.

Applications for any of the described systems herein, such as, e.g., system 10, system 10A, and system 10B, herein may include affecting growth and/or growth rate of animals and/or other organisms. For example, a particular type of animal may have a typical growth rate, or range of typical growth rates, under growing conditions that lack a significant electromagnetic effect and/or field. For the purposes of this description, a significant electromagnetic field may be determined as an electromagnetic field of at least a predetermined threshold level of tesla. The predetermined threshold may be 1 pT, 1 nT, 1 mT, 10 mT, 100 mT, and/or another threshold. Using any of the electrical systems described herein, the growth rate, or range of typical growth rates, of the particular type of animal may be increased to a higher growth rate, or higher range of growth rates, for the particular animal. A unit of growth rate may be inch/day, or another unit expressing some length, area, volume, or size per unit of time, and/or another appropriate unit.

For example, a specific type of animal may have a typical maximum growth level, under growing conditions that lack a significant electromagnetic field. Using any of the electrical systems described herein, the maximum growth level, or range of typical maximum growth levels, of the specific type of animal may be increased to a higher maximum growth level, or higher range of maximum growth levels, for the specific animal. Maximum growth level may be expressed in inches, square inches, liters, kilograms, lipid content, and/or another unit expressing some length, area, volume, weight, or size, and/or another appropriate unit.

For example, a particular type of animal may have a typical maximum yield, under growing conditions that lack a significant electromagnetic field. Using any of the electrical systems described herein, the maximum yield, or range of typical maximum yields, of the particular type of animal may be increased to a higher maximum yield, or higher range of maximum yields, for the particular animal. Maximum yield may be expressed in volume or weight per area and/or period, such as kilogram/square feet, or pounds per acre per week, and/or other units as appropriate.

For example, a particular type of animal may have a typical duration to reach maturity, under growing conditions that lack a significant electromagnetic field. Using any of the electrical systems described herein, the duration to reach maturity, or range of typical durations to reach maturity, of the particular type of animal may be decreased to a shorter duration to reach maturity, or shorter range of duration to reach maturity, for the particular animal. Duration to reach maturity may be expressed in hours, days, weeks, and/or other units as appropriate.

Figure 2:
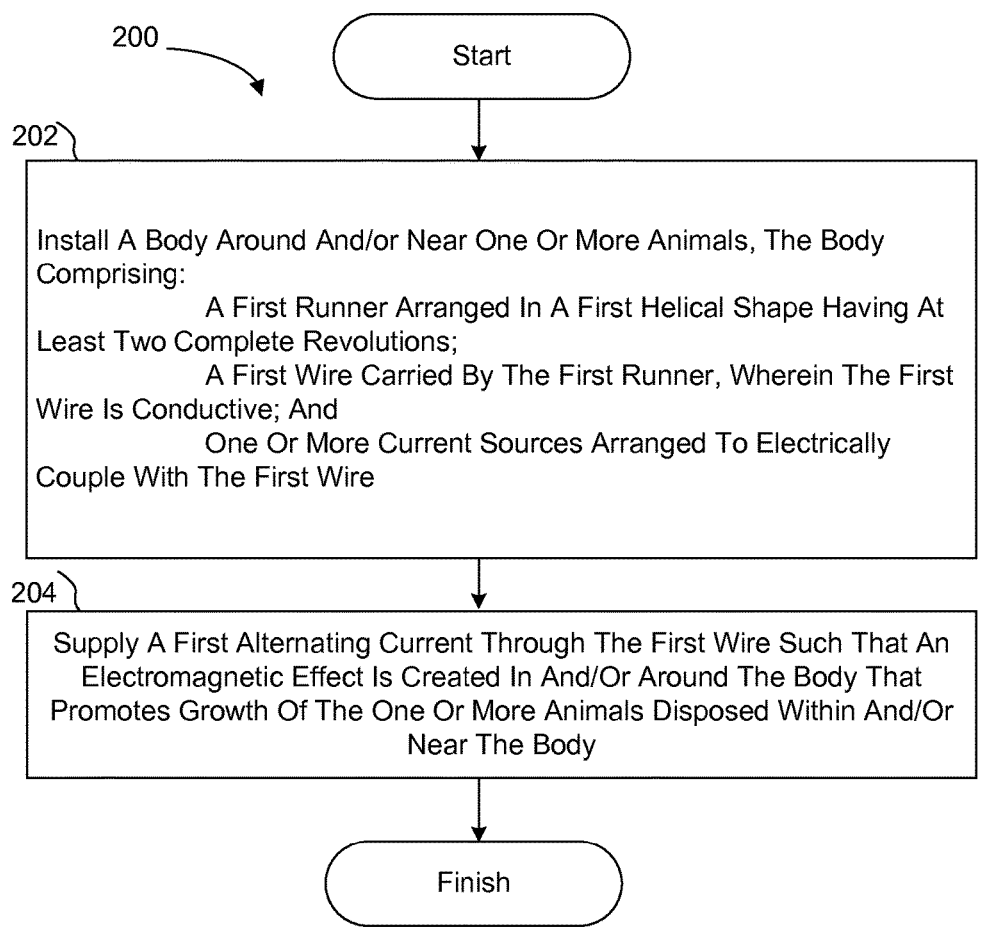
FIG. 2 illustrates a method for promoting growth of an animal, according to one or more implementations.

FIG. 2 illustrates a method 200 for promoting growth of one or more animals. The operations of method 200 presented below are intended to be illustrative. In certain implementations, method 200 may be accomplished with one or more additional operations not described, and/or without one or more of the operations discussed. Additionally, the order in which the operations of method 200 are illustrated in FIG. 2 and described below is not intended to be limiting.

In certain implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 300.

At an operation 202, a body is installed around and/or near one or more animals. The body includes at least one runner, a wire, and one or more current sources. The runner is arranged in a helical shape having at least two complete revolutions. The wire is carried by the first runner. The wire is conductive. The one or more current sources are arranged to electrically couple with the wire. In one implementation, operation 202 is performed by a user of system 10 (shown in FIG. 1 and described above).

At an operation 204, an alternating current is supplied through the wire such that an electromagnetic effect (e.g. an electromagnetic field) is created in and/or around the body that promotes growth of the one or more animals disposed within and/or near the body. In one implementation, operation 204 is performed by one or more current sources similar to or substantially the same as current source 11 (shown in FIG. 1 and described above).

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any implementation can be combined with one or more features of any other implementation.

What is claimed is:

1. An electrical system for promoting growth of one or more animals, the system comprising:
    a body comprising
        a first runner arranged in a first helical shape having at least two complete revolutions, wherein the body is configured to be installed around and/or near the one or more animals, and
        a second runner arranged in a second helical shape having at least two complete revolutions,
            wherein the first runner and the second runner are intertwined in a shape of a double helix;
    a first wire carried by the first runner, wherein the first wire is conductive,
        wherein the first wire comprises a pair of twisted wires, and
        wherein the first wire is arranged at a fixed and constant distance from a surface of the first runner for individual ones of the revolutions;
    a second wire carried by the second runner, wherein the second wire is conductive,
        wherein the second wire comprises a second pair of twisted wires, and
        wherein the second wire is arranged at a fixed and constant distance from a surface of the second runner for individual ones of the revolutions; and
    one or more current sources arranged to electrically couple with the first wire and the second wire, wherein the one or more current sources are configured to
        supply a first alternating current through the first wire such that an electromagnetic effect is created in and/or around the body that promotes growth of the one or more animals disposed within and/or near the body, and
        supply a second alternating current through the second wire such that the electromagnetic effect is modified,
    wherein said first current and said second current are two independent currents, and
    wherein the body is configured to be installed around an area having a width and a length, wherein the width is between 10 and 200 feet, and wherein the length is between 20 and 500 feet.

2. The system of claim 1, wherein the one or more animals comprise one or more of a chicken, a cow, a pig, a lamb, a goat, a bird, a fish, a crustacean, a mollusk, and/or a reptile.

3. The system of claim 1, wherein the one or more animals comprise one or more animals that are raised, bred, grown, or produced in captivity for a commercial purpose.

4. The system of claim 1, wherein the body is arranged in a toroidal shape.

5. The system of claim 1, wherein the first wire is spirally wound around the first runner of the body such that the first wire is arranged in a helical shape having an axis that coincides with the first runner.

6. The system of claim 1, wherein the first wire is spirally wound around the first runner of the body such that the first wire is arranged in a helical shape formed around the first helical shape of the first runner.

7. The system of claim 1, wherein the first runner is arranged in between 2 and 10000 revolutions.

8. The system of claim 1, wherein the first wire is wound around the first runner in between 2 and 10000 revolutions per revolution of the first helical shape of the first runner.

9. The system of claim 1, wherein the electromagnetic effect is an electromagnetic field having one or more frequencies, wherein the one or more frequencies are above 0 Hz and below 40 GHz.

10. The system of claim 1, wherein the first alternating current, has one or more frequencies between 0 Hz and 20 kHz.

11. The system of claim 1, further comprising:
one or more physical processors configured to execute computer program components, wherein the computer program components comprise:
a sound input component that obtains sound information, wherein the sound information comprises at least one or more sound signals, and wherein the sound signals have at least one of one or more specific frequencies, one or more waveforms, and one or more wave shapes, and
a playback component that produces one or more sound signals based on the obtained sound information;
wherein the one or more current sources are further configured to supply the first alternating current such that the first alternating current corresponds to the one or more produced sound signals.

12. The system of claim 11, wherein the computer program components further comprises a processing component that processes the obtained sound information from the sound input component,
wherein the processing component generates a processed signal based on the obtained sound information by one or more of converting, filtering modifying and transforming the obtained sound information, and
wherein the playback component produces one or more sound signals based on the processed signal.

13. A method for promoting growth of one or more animals, the method comprising:
installing a body around and/or near the one or more animals, the body comprising:
a first runner arranged in a first helical shape having at least two complete revolutions;
a second runner arranged in a second helical shape having at least two complete revolutions,
wherein the first runner and the second runner are intertwined in a shape of a double helix;
a first wire carried by the first runner, wherein the first wire is conductive,
wherein the first wire comprises a pair of twisted wires, and
wherein the first wire is arranged at a fixed and constant distance from a surface of the first runner for individual ones of the revolutions;
a second wire carried by the second runner, wherein the second wire is conductive,
wherein the second wire comprises a second pair of twisted wires, and
wherein the second wire is arranged at a fixed and constant distance from a surface of the second runner for individual ones of the revolutions; and
one or more current sources arranged to electrically couple with the first wire and the second wire;
supplying a first alternating current through the first wire such that an electromagnetic effect is created in and/or around the body that promotes growth of the one or more animals disposed within and/or near the body; and
supplying a second alternating current through the second wire such that the electromagnetic effect is modified,
wherein said first current and said second current are two independent currents, and
wherein installing the body comprises installing the body around an area having a width and a length, wherein the width is between 10 and 200 feet, and wherein the length is between 20 and 500 feet.

14. The method of claim 13, wherein the one or more animals comprise one or more of a chicken, a cow, a pig, a lamb, a goat, a bird, a fish, a crustacean, a mollusk, and/or a reptile.

15. The method of claim 13, wherein the one or more animals comprise one or more animals that are raised, bred, grown, or produced in captivity for a commercial purpose.

16. The method of claim 13, wherein installing the body comprises arranging the body in a toroidal shape.

17. The method of claim 13, wherein installing the body comprises spirally winding the first wire around the first runner of the body such that the first wire is arranged in a helical shape having an axis that coincides with the first runner.

18. The method of claim 13, wherein installing the body comprises spirally winding the first wire around the first runner of the body such that the first wire is arranged in a helical shape formed around the first helical shape of the first runner.

19. The method of claim 13, wherein installing the body comprises arranging the first runner in between 2 and 10000 revolutions.

20. The method of claim 13, wherein installing the body comprises winding the first wire around the first runner in between 2 and 10000 revolutions per revolution of the first helical shape of the first runner.

21. The method of claim 13, wherein supplying the first alternating current is accomplished such that the electromagnetic effect is an electromagnetic field having one or more frequencies, wherein the one or more frequencies are above 0 Hz and below 40 GHz.

22. The method of claim 13, supplying the first alternating current is accomplished such that the first alternating current has one or more frequencies between 0 Hz and 20 kHz.

23. The method of claim 13, further comprising:
obtaining sound information, wherein the sound information comprises at least one or more sound signals, and wherein the sound signals have at least one of one or more specific frequencies, one or more waveforms, and one or more wave shapes, and
producing one or more sound signals based on the obtained sound information;
wherein supplying the first alternating current is accomplished such that the first alternating current corresponds to the one or more produced sound signals.

24. The system of claim 23, further comprising
processing the obtained sound information from the sound input component, generating a processed signal based on the obtained sound information by one or more of converting, filtering modifying and transforming the obtained sound information, and producing one or more sound signals based on the processed signal.

25. The method of claim 13, wherein the one or more animals have a typical growth rate under growing conditions that lack the electromagnetic effect, and wherein promotion of growth comprises a faster growth rate than the typical growth rate.

26. The method of claim 13, wherein the one or more animals have a typical maximum growth level under growing conditions that lack the electromagnetic effect, and wherein promotion of growth comprises a maximum growth level greater than the typical maximum growth level.

27. The method of claim 13, wherein the one or more animals have a typical maximum yield under growing conditions that lack the electromagnetic effect, and wherein promotion of growth comprises a maximum yield greater than the typical maximum yield.

28. The method of claim 13, wherein the one or more animals have a typical duration to reach maturity under growing conditions that lack the electromagnetic effect, and wherein promotion of growth comprises a duration to reach maturity shorter than the typical duration to reach maturity.

29. An electrical system for promoting growth of one or more animals, the system comprising:

a set of bodies, wherein individual bodies from the set of bodies comprise a first runner arranged in a helical shape having at least two complete revolutions, and a second runner arranged in a second helical shape having at least two complete revolutions, wherein the set of bodies is installed around an area having a width and a length, wherein the width is between 8 and 100 feet, and wherein the length is between 10 and 500 feet;

a set of wires, wherein individual wires from the set of wires are carried by individual runners included in the set of bodies, wherein individual wires from the set of wires are conductive, such that a first wire of the set of wires is carried by the first runner and comprises a pair of twisted wires, wherein the first wire is arranged at a fixed and constant distance from a surface of the first runner for individual ones of the revolutions, and a second wire of the set of wires carried by the second runner and comprises a second pair of twisted wires, wherein the second wire is arranged at a fixed and constant distance from a surface of the second runner for individual ones of the revolutions; and one or more current sources arranged to electrically couple with individual wires from the set of wires, wherein the one or more current sources are configured to supply at least two alternating currents through individual wires from the set of wires, such that at least a first alternating current is supplied through the first wire such that one or more electromagnetic fields are created near the set of bodies, wherein the one or more electromagnetic fields promote growth of one or more animals disposed in the area, and such that at least a second alternating current is supplied through the second wire.

* * * * *